United States Patent
Hachigo et al.

(10) Patent No.: US 8,177,911 B2
(45) Date of Patent: May 15, 2012

(54) DAMAGE EVALUATION METHOD OF COMPOUND SEMICONDUCTOR MEMBER, PRODUCTION METHOD OF COMPOUND SEMICONDUCTOR MEMBER, GALLIUM NITRIDE COMPOUND SEMICONDUCTOR MEMBER AND GALLIUM NITRIDE COMPOUND SEMICONDUCTOR MEMBRANE

(75) Inventors: Akihiro Hachigo, Itami (JP); Takayuki Nishiura, Itami (JP)

(73) Assignee: Sumitomo Electric Industries, Ltd., Osaka (JP)

( * ) Notice: Subject to any disclaimer, the term of this patent is extended or adjusted under 35 U.S.C. 154(b) by 0 days.

(21) Appl. No.: 11/907,322

(22) Filed: Oct. 11, 2007

(65) Prior Publication Data

US 2008/0044338 A1   Feb. 21, 2008

Related U.S. Application Data

(62) Division of application No. 11/446,976, filed on Jun. 6, 2006, now abandoned.

(30) Foreign Application Priority Data

Jun. 6, 2005 (JP) ................................. P2005-165957

(51) Int. Cl.
*C30B 29/14* (2006.01)

(52) U.S. Cl. ............. 117/86; 117/87; 117/88; 117/952

(58) Field of Classification Search ............ 117/86, 117/87, 88, 952
See application file for complete search history.

(56) References Cited

U.S. PATENT DOCUMENTS

| | | | |
|---|---|---|---|
| 4,492,871 A | | 1/1985 | Tajima |
| 5,602,418 A | * | 2/1997 | Imai et al. ................. 257/627 |
| 6,156,581 A | * | 12/2000 | Vaudo et al. ............... 438/22 |
| 6,579,068 B2 | * | 6/2003 | Bridger et al. .............. 417/53 |
| 6,686,608 B1 | * | 2/2004 | Takahira .................. 257/96 |
| 6,780,239 B2 | * | 8/2004 | Sarayama et al. ............ 117/36 |
| 7,053,420 B2 | * | 5/2006 | Tadatomo et al. ........... 257/98 |
| 7,357,882 B2 | * | 4/2008 | Seto et al. .............. 252/301.4 R |
| 2002/0066319 A1 | * | 6/2002 | Beach et al. ............... 73/754 |
| 2002/0071785 A1 | * | 6/2002 | Beach et al. ............ 422/82.05 |
| 2005/0030995 A1 | * | 2/2005 | Kawakami et al. ........... 372/43 |
| 2006/0192218 A1 | * | 8/2006 | Kyono et al. ................ 257/96 |
| 2006/0272573 A1 | * | 12/2006 | Hachigo et al. ............. 117/88 |

FOREIGN PATENT DOCUMENTS

GB      2 306 640 A      5/1997

(Continued)

OTHER PUBLICATIONS

Zhao Yi-guang et al Ge Related-Defect Energy and Microcavity Effect in GaN Epitaxial Layer CHIN.PHYS.LETT. vol. 15, No. 9 (1998) 674-676.*

(Continued)

*Primary Examiner* — Bob M Kunemund

(74) *Attorney, Agent, or Firm* — McDermott Will & Emery LLP

(57) ABSTRACT

A method of evaluating damage of a compound semiconductor member, comprising: a step of performing measurement of photoluminescence on a surface of the compound semiconductor member; and a step of evaluating damage on the surface of the compound semiconductor member, using a half width of a peak at a wavelength corresponding to a bandgap of the compound semiconductor member, in an emission spectrum obtained by the measurement of photoluminescence.

6 Claims, 9 Drawing Sheets

FOREIGN PATENT DOCUMENTS

| | | |
|---|---|---|
| JP | 01-278025 | 11/1989 |
| JP | 03-001553 | 1/1991 |
| JP | 08-203837 | 8/1996 |
| JP | 09-008356 | 1/1997 |
| JP | 09-246341 | 9/1997 |
| JP | 2003-133246 | 5/2003 |
| WO | WO 03/077391 A1 | 9/2003 |

OTHER PUBLICATIONS

European Search Report issued in European Patent Application No. EP 06009693.0-1234/1731897, dated Mar. 3, 2009.

Santhanaraghavka, P. et al., "Photoluminescence Investigations on Liquid Encapsulated Czochralski Grown Gallium Arsenide," Physica Status Solidi (A), Applied Research, Berlin, DE, vol. 142, 1994, pp. 121-126, XP007907204.

Qian, Y.H. et al., "Electrical and optical characterization of extended defects in SIMOX structures," Semiconductor Science and Technology, IOP. Bristol, GB, vol. 11, No. 1, 1996, pp. 27-33, XP000545072.

Shi, S. S. et al., "Photoluminescence study of hydrogenated aluminum oxide-semiconductor interface," Applied Physics Letters, American Institute of Physics, Melville, NY, vol. 70, No. 10, 1997, pp. 1293-1295, XP000685292.

Liu, D. W. et al., "Photoluminescence-excitation-correlation spectroscopic study of a high-density two-dimensional electron gas in GaAs/Al0.3Ga0.7As modulation-doped quantum well," Physical Review, B. Condensed Matter, American Institute of Physics, New York, vol. 49, No. 7, 1994, pp. 4640-4645, XP000430280.

Chinese Office Action, w/ English translation thereof, issued in Chinese Patent Application No. CN 2006100887044 dated Mar. 13, 2009.

United States Office Action issued in U.S. Appl. No. 11/446,976, dated Mar. 17, 2009.

European Search Report issued in European Patent Application No. 06009693.0, mailed Jun. 24, 2009.

Schuck, P.J., et al., "Cross-sectional imaging of pendeo-epitaxial GaN using continuous-wave two-photon microphotoluminescence", Applied Physics Letters, Sep. 9, 2002, vol. 81, No. 11, American Institute of Physics.

United States Office Action issued in U.S. Appl. No. 11/446,976, dated Oct. 29, 2009.

Japanese Notice of Reasons for Rejection, w/ English translation thereof, issued in Japanese Patent Application No. JP 2005-165957 dated Oct. 20, 2009.

Japanese Notification of Information Provision, w/ English translation thereof, issued in Japanese Patent Application No. JP 2009-281791 dated Jun. 28, 2011.

I. Shalish et al., "Surface states and surface oxide in GaN layers," Journal of Applied Physics, vol. 89, No. 1, Jan. 1, 2001, pp. 390-395.

Japanese Office Action issued in Japanese Patent Application No. JP 2005-165957 dated Aug. 16, 2011.

Japanese Office Action, w/ English translation thereof, issued in Japanese Patent Application No. JP 2005-165957 dated Sep. 14, 2010.

* cited by examiner

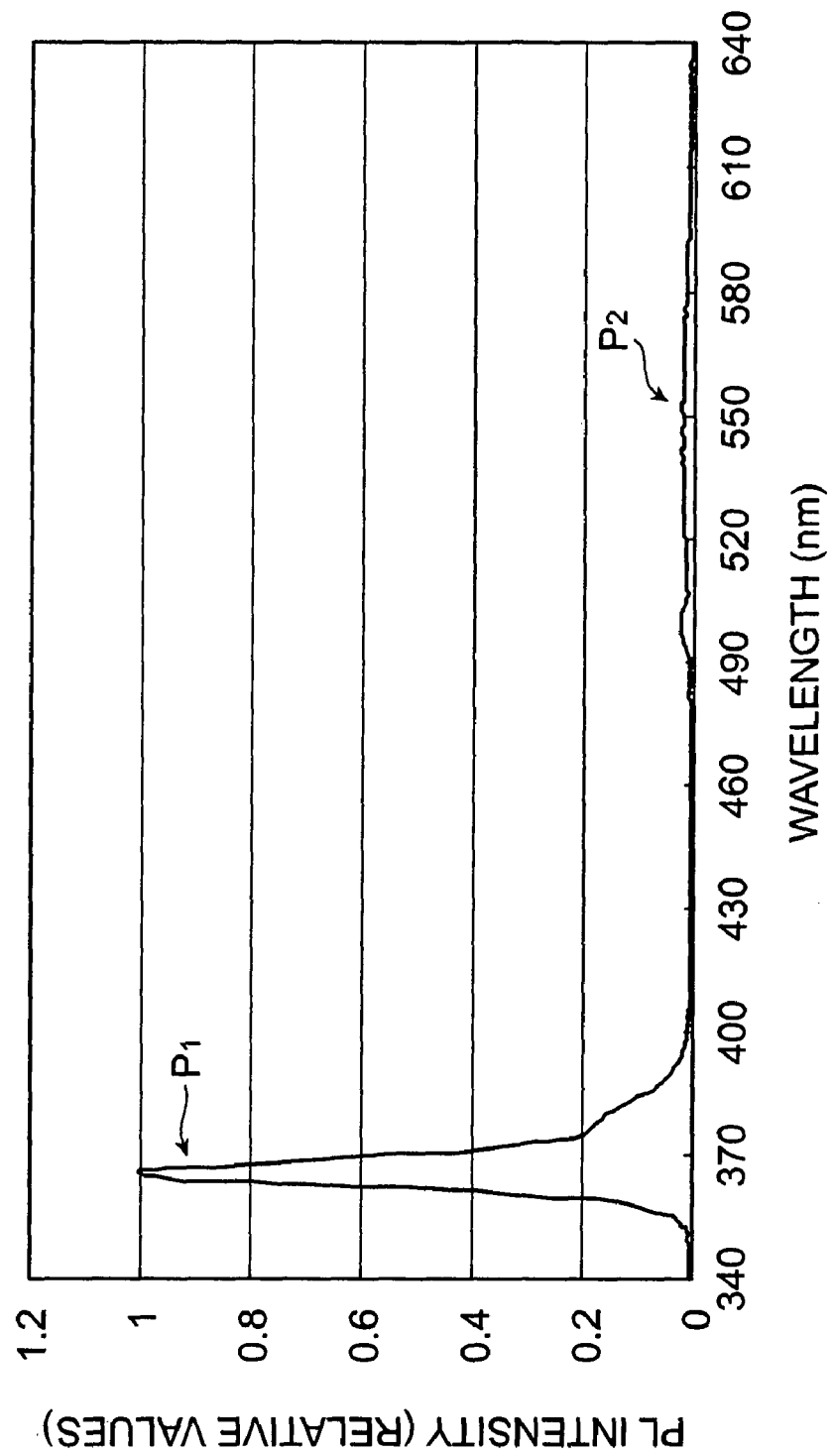

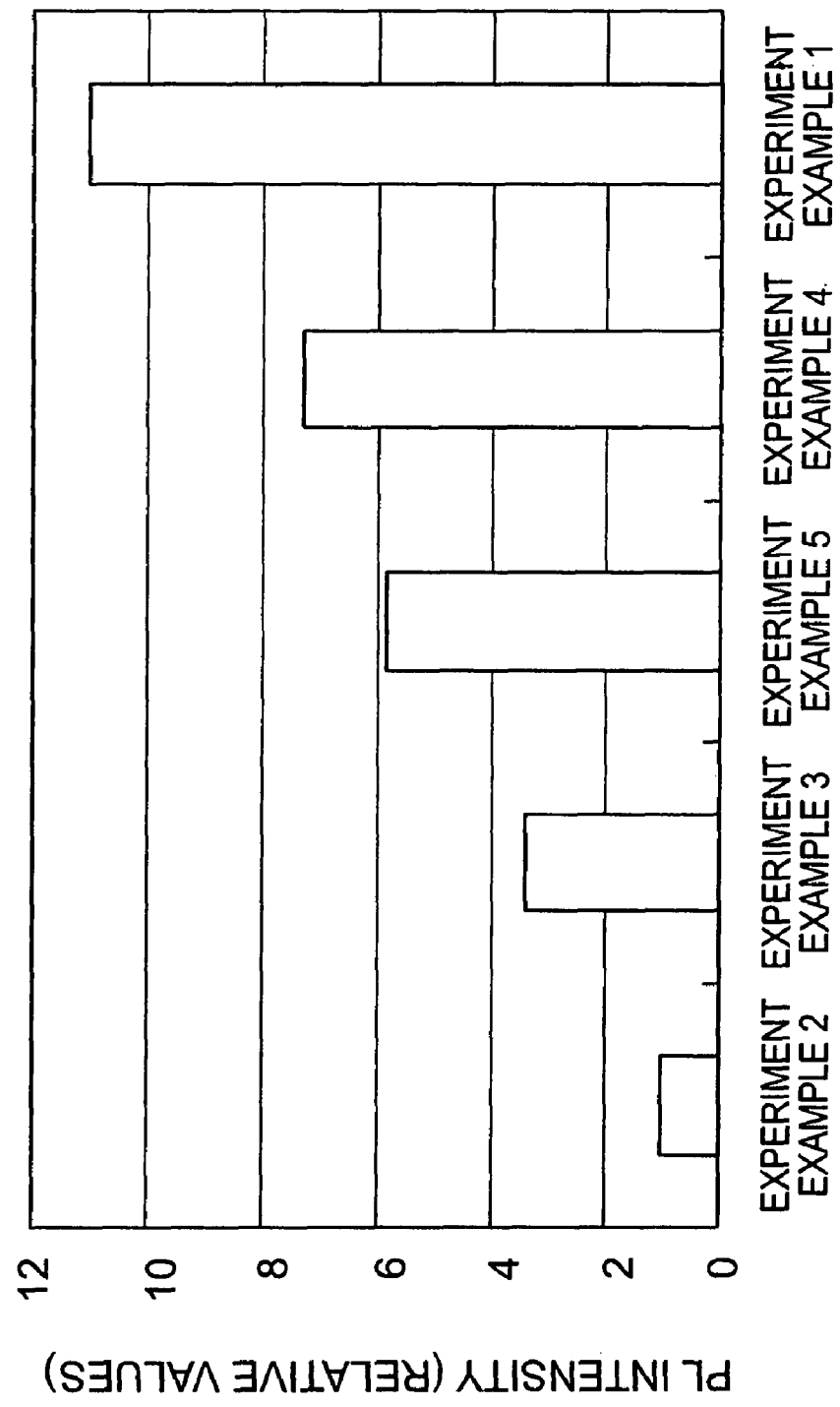

DAMAGE EVALUATION METHOD OF COMPOUND SEMICONDUCTOR MEMBER, PRODUCTION METHOD OF COMPOUND SEMICONDUCTOR MEMBER, GALLIUM NITRIDE COMPOUND SEMICONDUCTOR MEMBER AND GALLIUM NITRIDE COMPOUND SEMICONDUCTOR MEMBRANE

This application is a Divisional of U.S. application Ser. No. 11/446,976, filed Jun. 6, 2006 now abandoned, claiming priority of Japanese Application No. P2005-165957, filed Jun. 6, 2005, the entire contents of each of which are hereby incorporated by reference.

BACKGROUND OF THE INVENTION

1. Field of the Invention

The present invention relates to a damage evaluation method of a compound semiconductor member, a production method of a compound semiconductor member, a gallium nitride compound semiconductor member, and a gallium nitride compound semiconductor membrane.

2. Related Background Art

Compound semiconductors have various merits in comparison with Si. For example, the compound semiconductors permit control of the bandgap through adjustment of compositions. Furthermore, the compound semiconductors have such optical properties as direct transition and wide bandgap, and are thus suitably applied to optical devices such as LEDs or LDs. Since the compound semiconductors have high carrier mobility, they are also suitably applied to high-speed devices.

In producing such compound semiconductor devices as the optical devices or high-speed devices, a substrate used is a compound semiconductor substrate, or a laminated substrate in which a compound semiconductor membrane is formed on an amorphous substrate such as a glass substrate. For example, a compound semiconductor membrane or electrodes are formed on a surface of the compound semiconductor substrate or laminated substrate. The device characteristics of the compound semiconductor devices are significantly affected by an interface between the compound semiconductor substrate or laminated substrate and the compound semiconductor membrane or by interfaces between the compound semiconductor substrate or laminated substrate and the electrodes. Therefore, it is important to evaluate the interfaces in the compound semiconductor devices.

In production of the compound semiconductor devices, damage occurs on the foregoing interfaces in several production processes. For example, since surface roughness of the compound semiconductor substrate or laminated substrate affects the device characteristics, the surface of the compound semiconductor substrate or laminated substrate is subjected to polishing or etching. This process produces scratches or distortion on the surface to cause damage on the surface. For example, dry etching or wet etching or the like is used in forming a thin film or fine pattern of nanometer size on the surface of the compound semiconductor substrate or laminated substrate. At this time, damage is caused on the surface of the compound semiconductor substrate or laminated substrate or on the surface of the thin film or fine pattern.

When a compound semiconductor device is produced, for example, by growing an epitaxial film on the surface of the compound semiconductor substrate or compound semiconductor membrane with the surface including the damage as described above, the device characteristics are degraded by virtue of the damage existing at the interface between the compound semiconductor substrate or compound semiconductor membrane and the epitaxial film.

Methods for evaluating the damage on the surface of the compound semiconductor substrate or compound semiconductor membrane include methods using X-ray diffraction, scanning electron microscope (SEM), cathodoluminescence, or the like as usually adopted methods.

On the other hand, Japanese Patent Application Laid-Open No. 9-246341 discloses a method of evaluating damage on a semiconductor wafer by a photoluminescence method.

SUMMARY OF THE INVENTION

However, the method disclosed in the foregoing Patent Application is not always satisfactory for performing detailed evaluation of a level of damage.

An object of the present invention is therefore to provide a damage evaluation method of a compound semiconductor member permitting detailed evaluation of a level of damage on a surface and a production method of a compound semiconductor member with a low level of damage, and to provide a gallium nitride compound semiconductor member and a gallium nitride compound semiconductor membrane with a low level of damage.

In order to solve the above problem, a damage evaluation method of a compound semiconductor member according to the present invention is a method of evaluating damage of a compound semiconductor member, comprising: a step of performing measurement of photoluminescence on a surface of the compound semiconductor member; and a step of evaluating damage on the surface of the compound semiconductor member, using a half width of a peak at a wavelength corresponding to a bandgap of the compound semiconductor member, in an emission spectrum obtained by the measurement of photoluminescence.

Another damage evaluation method of a compound semiconductor member according to the present invention is a method of evaluating damage of a compound semiconductor member, comprising: a step of performing measurement of photoluminescence on a surface of the compound semiconductor member; and a step of evaluating damage on the surface of the compound semiconductor member, using an intensity of a peak located on a longer wavelength side than a wavelength corresponding to a bandgap of the compound semiconductor member, in an emission spectrum obtained by the measurement of photoluminescence.

Another damage evaluation method of a compound semiconductor member according to the present invention is a method of evaluating damage of a compound semiconductor member, comprising: a step of performing measurement of photoluminescence on a surface of the compound semiconductor member; and a step of evaluating damage on the surface of the compound semiconductor member, using a half width of a peak located on a longer wavelength side than a wavelength corresponding to a bandgap of the compound semiconductor member, in an emission spectrum obtained by the measurement of photoluminescence.

Another damage evaluation method of a compound semiconductor member according to the present invention is a method of evaluating damage of a compound semiconductor member, comprising: a step of performing measurement of photoluminescence on a surface of the compound semiconductor member; and a step of evaluating damage on the surface of the compound semiconductor member, using a ratio of an intensity of a peak at a wavelength corresponding to a bandgap of the compound semiconductor member to an intensity of a peak located on a longer wavelength side than the wavelength corresponding to the bandgap, in an emission spectrum obtained by the measurement of photoluminescence.

The compound semiconductor member is preferably a compound semiconductor substrate. The compound semiconductor member is preferably a compound semiconductor membrane provided on a substrate. The compound semiconductor member is preferably comprised of either one of monocrystalline material and polycrystalline material. The bandgap is preferably not less than $1.6 \times 10^{-19}$ J.

The compound semiconductor member is preferably comprised of a nitride compound semiconductor containing at least one of B, Al, and Ga. The compound semiconductor member is preferably comprised of an oxide compound semiconductor containing, at least one of Be and Zn. Furthermore, the compound semiconductor member is preferably comprised of a ZnSe compound semiconductor.

A production method of a compound semiconductor member according to the present invention is a method of producing a compound semiconductor member, comprising: a step of performing measurement of photoluminescence on a surface of the compound semiconductor member; and a step of determining that the compound semiconductor member is nondefective when a half width of a peak at a wavelength corresponding to a bandgap of the compound semiconductor member in an emission spectrum obtained by the measurement of photoluminescence is not more than a predetermined threshold.

Another production method of a compound semiconductor member according to the present invention is a method of producing a compound semiconductor member, comprising: a step of performing measurement of photoluminescence on a surface of the compound semiconductor member; and a step of determining that the compound semiconductor member is nondefective when an intensity of a peak at a wavelength corresponding to a bandgap of the compound semiconductor member in an emission spectrum obtained by the measurement of photoluminescence is not less than a predetermined threshold with respect to an intensity of a peak at the wavelength in an emission spectrum obtained by measurement of photoluminescence on a surface of a compound semiconductor member without damage.

Another production method of a compound semiconductor member according to the present invention is a method of producing a compound semiconductor member, comprising: a step of performing measurement of photoluminescence on a surface of the compound semiconductor member; and a step of determining that the compound semiconductor member is nondefective when a half width of a peak on a longer wavelength side than a wavelength corresponding to a bandgap of the compound semiconductor member in an emission spectrum obtained by the measurement of photoluminescence is not more than a predetermined threshold.

Another production method of a compound semiconductor member according to the present invention is a method of producing a compound semiconductor member, comprising: a step of performing measurement of photoluminescence on a surface of the compound semiconductor member; and a step of determining that the compound semiconductor member is nondefective when a ratio of an intensity of a peak at a wavelength corresponding to a bandgap of the compound semiconductor member to an intensity of a peak located on a longer wavelength side than the wavelength corresponding to the bandgap in an emission spectrum obtained by the measurement of photoluminescence is not less than a predetermined threshold.

The compound semiconductor member is preferably a compound semiconductor substrate. The compound semiconductor member is preferably a compound semiconductor membrane provided on a substrate.

The production methods of the compound semiconductor member preferably further comprise a step of forming a thin film on the surface of the compound semiconductor member, after the step of determining that the compound semiconductor member is nondefective.

The production methods of the compound semiconductor member preferably further comprise a step of forming an electrode on the surface of the compound semiconductor member, after the step of determining that the compound semiconductor member is nondefective.

A gallium nitride compound semiconductor member according to the present invention is a gallium nitride compound semiconductor member wherein in an emission spectrum obtained by measurement of photoluminescence on a surface of the gallium nitride compound semiconductor member, an intensity of a peak at a wavelength corresponding to a bandgap of the gallium nitride compound semiconductor member is not less than twice an intensity of a peak located on a longer wavelength side than the wavelength corresponding to the bandgap.

Another gallium nitride compound semiconductor member according to the present invention is a gallium nitride compound semiconductor member wherein in an emission spectrum obtained by measurement of photoluminescence on a surface of the gallium nitride compound semiconductor member, an intensity of a peak at a wavelength corresponding to a bandgap of the gallium nitride compound semiconductor member is not less than $\frac{1}{10}$ of an intensity of a peak at the wavelength in an emission spectrum obtained by measurement of photoluminescence on a surface of a gallium nitride compound semiconductor member without damage.

The gallium nitride compound semiconductor member is preferably a gallium nitride compound semiconductor substrate. The gallium nitride compound semiconductor member is preferably a gallium nitride compound semiconductor membrane provided on a substrate.

A gallium nitride compound semiconductor membrane according to the present invention is a gallium nitride compound semiconductor membrane formed on a gallium nitride compound semiconductor member wherein in an emission spectrum obtained by measurement of photoluminescence on a surface of the gallium nitride compound semiconductor member, an intensity of a peak at a wavelength corresponding to a bandgap of the gallium nitride compound semiconductor member is not less than twice an intensity of a peak located on a longer wavelength side than the wavelength corresponding to the bandgap.

Another gallium nitride compound semiconductor membrane according to the present invention is a gallium nitride compound semiconductor membrane formed on a gallium nitride compound semiconductor member wherein in an emission spectrum obtained by measurement of photoluminescence on a surface of the gallium nitride compound semiconductor member, an intensity of a peak at a wavelength corresponding to a bandgap of the gallium nitride compound semiconductor member is not less than $\frac{1}{10}$ of an intensity of a peak at the wavelength in an emission spectrum obtained by measurement of photoluminescence on a surface of a gallium nitride compound semiconductor member without damage.

BRIEF DESCRIPTION OF THE DRAWINGS

FIG. 7 is a graph showing an emission spectrum obtained from a monocrystalline GaN substrate of Experiment Example 5.

FIG. 9 shows intensities of a peak near 365 nm in respective emission spectra obtained from monocrystalline GaN substrates of Experiment Example 1 to Experiment Example 5.

DESCRIPTION OF THE PREFERRED EMBODIMENTS

Embodiments of the present invention will be described below in detail with reference to the accompanying drawings. In the description of the drawings identical or equivalent elements will be denoted by the same reference symbols, without redundant description.

Figure 1:
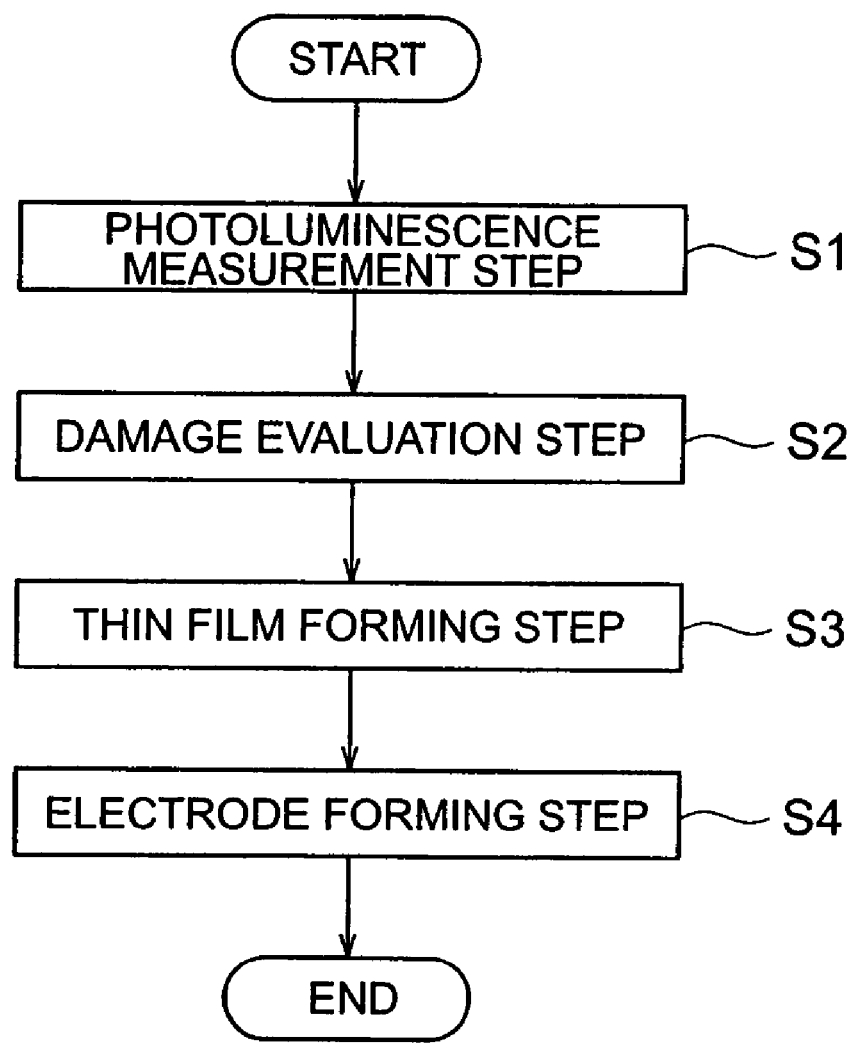
FIG. 1 is a flowchart showing steps in a damage evaluation method of a compound semiconductor member and in a production method of a compound semiconductor member according to an embodiment.

FIG. 1 is a flowchart showing steps in a damage evaluation method of a compound semiconductor member and in a production method of a compound semiconductor member according to an embodiment. The damage evaluation method of the compound semiconductor member according to the embodiment includes a photoluminescence measurement step S1 and a damage evaluation step S2. The production method of the compound semiconductor member according to the embodiment includes the photoluminescence measurement step S1 and damage evaluation step S2 and, preferably, further includes a thin film forming step S3 and an electrode forming step S4.

(Photoluminescence Measurement Step)

Figure 2:
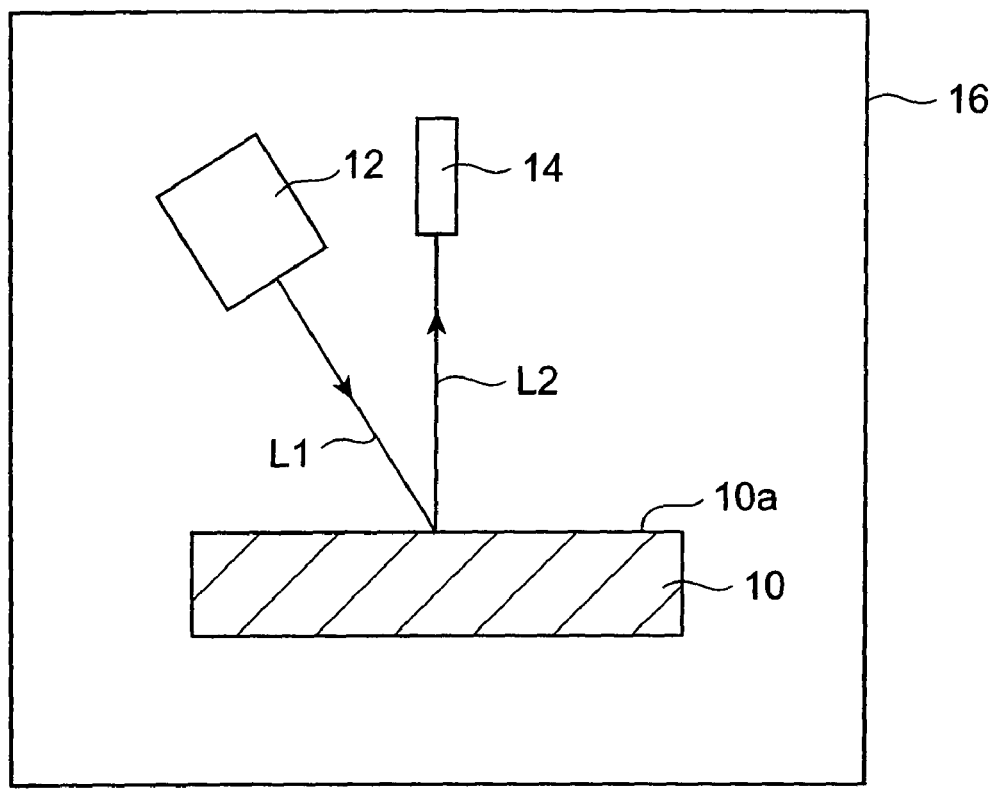
FIG. 2 is a drawing schematically showing a photoluminescence measurement step.

FIG. 2 is a drawing schematically showing the photoluminescence measurement step. The photoluminescence measurement step S1 is to perform measurement of photoluminescence on a surface 10a of a compound semiconductor substrate 10 (compound semiconductor member). The photoluminescence measurement is preferably carried out with a photoluminescence measurement device 16.

The photoluminescence measurement device 16 has a light source 12 for emitting light L1 toward the surface 10a of the compound semiconductor substrate 10. The energy of light L1 is set to be higher than the bandgap of the compound semiconductor substrate 10. As the light L1 impinges on the surface 10a, electrons are excited from the valence band to the conduction band and then return to the valence band to emit light L2 from the compound semiconductor substrate 10. When the light L2 enters a light detection unit 14, an emission spectrum is acquired.

The light L1 is preferably monochromatic laser light, but may include a plurality of wavelength components. For obtaining the light L1 containing a plurality of wavelength components, the light source 12 to be used is preferably a dye laser. The light L1 can be white light containing wavelength components with energy higher than the bandgap of the compound semiconductor substrate 10.

Since the compound semiconductor substrate 10 is a bulk, it will suffer little influence from other members, e.g. influence of the back surface of the compound semiconductor substrate 10 or influence of a jig for fixing the compound semiconductor substrate 10 even if the light L1 penetrates deep, for example, into the interior of the compound semiconductor substrate 10 in the photoluminescence measurement.

The bandgap of the compound semiconductor substrate 10 is preferably not less than $1.6 \times 10^{-19}$ J (1 eV). In this case, even if the compound semiconductor substrate 10 is heated by the light L1 during the photoluminescence measurement, the compound semiconductor substrate 10 will be less likely to be affected by heat. For this reason, the photoluminescence measurement can be performed without difficulty and with high accuracy.

The compound semiconductor substrate 10 is preferably comprised of a nitride compound semiconductor containing at least one of B, Al, and Ga. The compound semiconductor substrate 10 is preferably comprised of an oxide compound semiconductor containing at least one of Be and Zn. Furthermore, the compound semiconductor substrate 10 is preferably comprised of a ZnSe compound semiconductor. In all these cases, the bandgap of the compound semiconductor substrate 10 is increased, and thus the compound semiconductor substrate becomes less likely to be affected by heat in the photoluminescence measurement.

More specifically, the compound semiconductor substrate 10 is made, for example, of a III-V compound semiconductor such as GaAs or InP, a nitride compound semiconductor such as BN, GaN, AlN, or InN, a II-VI compound semiconductor such as ZnO or ZnS, an oxide compound semiconductor such as $Be_xO_y$, ZnO, $Ga_2O_3$, or $Al_2O_3$, a ZnSe compound semiconductor such as ZnSe, or a ternary compound semiconductor such as GaAlN or InGaN. These compound semiconductors may be doped with an impurity.

For example, in a case where the compound semiconductor substrate 10 is made of a gallium nitride compound semiconductor, the gallium nitride compound semiconductor suitably applicable is of the wurtzite structure or the zinc blende (cubic crystal) structure. In the case of the wurtzite structure, the surface 10a may be any one of the (0001) face called the C-plane, the (10-10) face called the M-plane, the (11-20) face called the A-plane, the (01-12) face called the R-plane, and the (10-11) face called the S-plane. The C-plane can be either a Ga plane consisting of Ga or an N plane consisting of N. Since the Ga plane is normally more resistant to etching, the surface 10a is preferably the Ga plane, but the surface 10a may be the N plane.

Figure 3:
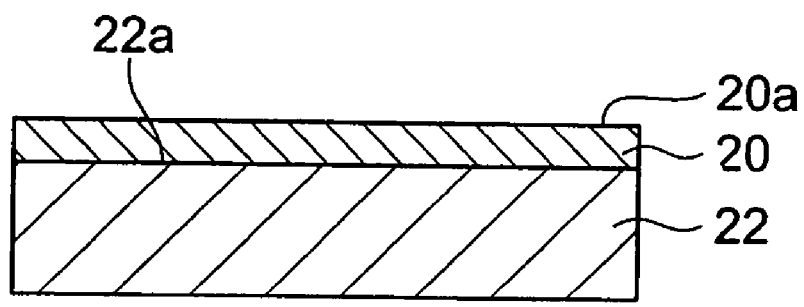
FIG. 3 is a sectional view schematically showing a compound semiconductor membrane provided on a substrate.

In performing the photoluminescence measurement, a compound semiconductor membrane 20 (compound semiconductor member) shown in FIG. 3 may also be used instead of the compound semiconductor substrate 10.

FIG. 3 is a sectional view schematically showing a compound semiconductor membrane provided on a substrate. The substrate 22 shown in FIG. 3 is, for example, an amorphous substrate such as a glass substrate, or a monocrystalline substrate such as a sapphire substrate or Si substrate. A constituent material of the compound semiconductor membrane 20 can be one of the materials listed for the compound semiconductor substrate 10.

In this case, the photoluminescence measurement is carried out by projecting the light L1 onto a surface 20a of the compound semiconductor membrane 20. If the light L1 is made incident from the direction perpendicular to the surface 20a, the light L2 can contain more information about the substrate 22, depending upon the film thickness of the compound semiconductor membrane 20. As the direction of incidence of the light L1 deviates from the direction perpendicular to the surface 20a, the information about the substrate 22 in the light L2 tends to decrease relatively.

(Damage Evaluation Step)

Figure 4:
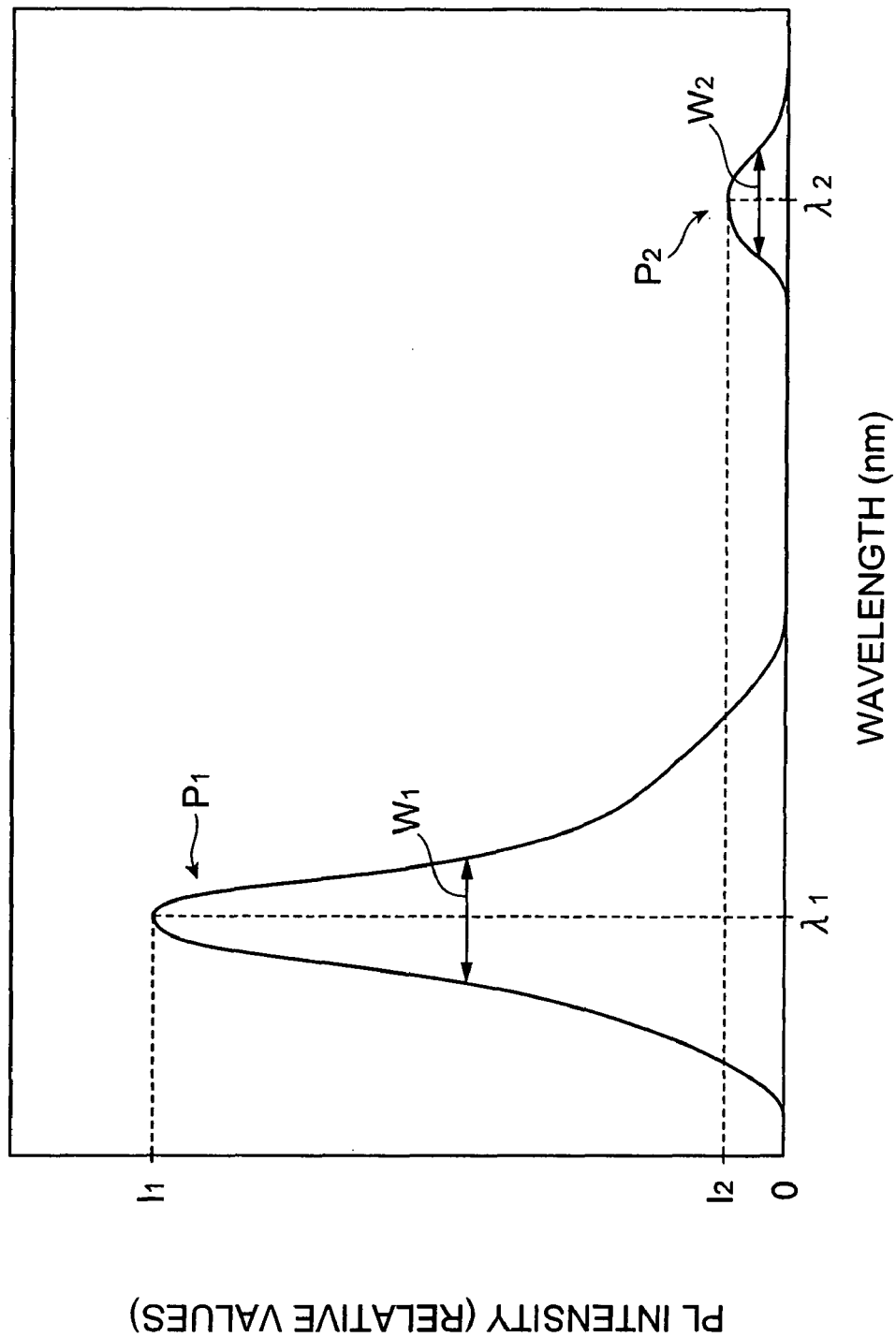
FIG. 4 is a drawing schematically showing an emission spectrum obtained by photoluminescence measurement.

FIG. 4 is a drawing schematically showing an emission spectrum obtained by the photoluminescence measurement. The damage evaluation step S2 is to evaluate damage on the surface 10a of the compound semiconductor substrate 10, using the emission spectrum obtained by the photoluminescence measurement. Examples of such damage include damage, scratches, distortion, or the like due to polishing, etching, or the like.

The emission spectrum shown in FIG. 4 has a peak $P_1$ at a wavelength $\lambda_1$ corresponding to the bandgap of the compound semiconductor substrate 10. The wavelength $\lambda_1$ has the same energy as the bandgap. The peak $P_1$ does not always have to be maximum at the wavelength $\lambda_1$. This emission spectrum also has a peak $P_2$ at a wavelength $\lambda_2$ located on the longer wavelength side than the wavelength $\lambda_1$. The peak $P_2$ does not always have to be maximum at the wavelength $\lambda_2$. The use of this emission spectrum enables detailed evaluation of damage on the surface 10a by Method 1 to Method 4 described below.

When the compound semiconductor substrate 10 is made, for example, of a monocrystalline material or polycrystalline material, the monocrystalline material or polycrystalline material turns into the amorphous form in a damaged region, and thus it becomes easier to discriminate the damaged region from the other region without damage. For this reason, damage becomes easier to detect, so that the accuracy of damage evaluation can be improved.

<Method 1>

Method 1 is to perform evaluation of damage using the half width $W_1$ of the peak $P_1$. Method 1 enables detailed damage evaluation as described below, using the half width $W_1$ of the peak $P_1$.

The half width $W_1$ of the peak $P_1$ varies with change in the spread of the band of the compound semiconductor substrate 10. Here the spread of the band varies with change in the interatomic distance between atoms constituting the compound semiconductor substrate 10. The interatomic distance varies depending upon the level of damage on the surface 10a. Therefore, the level of damage can be evaluated in detail by use of the half width $W_1$ of the peak $P_1$. For example, the half width $W_1$ of the peak $P_1$ tends to increase with increasing level of damage.

Method 1 is suitably applicable to production of compound semiconductor substrate 10. The compound semiconductor substrate 10 is determined to be nondefective when the half width $W_1$ of the peak $P_1$ is not more than a predetermined threshold; this permits the compound semiconductor substrate 10 with a low level of damage to be produced at a high yield.

<Method 2>

Method 2 is to perform evaluation of damage using the intensity $I_2$ of the peak $P_2$. Method 2 enables detailed damage evaluation as described below, using the intensity $I_2$ of the peak $P_2$.

The peak $P_2$ arises from energy levels appearing between bands of the compound semiconductor substrate 10. Therefore, the peak $P_2$ appears if damage to induce emission of light exists in the compound semiconductor substrate 10. Since the intensity $I_2$ of the peak $P_2$ varies depending upon the level of damage to induce emission of light, the level of damage can be evaluated in detail by use of the intensity $I_2$ of the peak $P_2$. For example, the intensity $I_2$ of the peak $P_2$ tends to increase with increasing level of damage.

Method 2 is suitably applicable to production of compound semiconductor substrate 10. The compound semiconductor substrate 10 is determined to be nondefective when the intensity $I_2$ of the peak $P_2$ is not more than a predetermined threshold, relative to an intensity of a peak located at the wavelength $\lambda_2$ in an emission spectrum obtained by photoluminescence measurement on a surface of a compound semiconductor substrate from which damage is preliminarily eliminated; this permits the compound semiconductor substrate 10 with a low level of damage to be produced at a high yield.

<Method 3>

Method 3 is to perform evaluation of damage using the half width $W_2$ of the peak $P_2$. Method 3 enables detailed damage evaluation as described below, using the half width $W_2$ of the peak $P_2$.

Since the half width $W_2$ of the peak $P_2$ varies according to the level of damage to induce emission of light, the level of damage can be evaluated in detail by use of the half width $W_2$ of the peak $P_2$. For example, the half width $W_2$ of the peak $P_2$ tends to increase with increasing level of damage.

Method 3 is suitably applicable to production of compound semiconductor substrate 10. The compound semiconductor substrate 10 is determined to be nondefective when the half width $W_2$ of the peak $P_2$ is not more than a predetermined threshold; this permits the compound semiconductor substrate 10 with a low level of damage to be produced at a high yield.

<Method 4>

Method 4 is to perform evaluation of damage using an intensity ratio $(I_1/I_2)$ of the intensity $I_1$ of the peak $P_1$ to the intensity $I_2$ of the peak $P_2$. Method 4 enables detailed damage evaluation as described below, using the intensity ratio $(I_1/I_2)$.

The intensity ratio $(I_1/I_2)$ can be an index of relationship between the level of damage to change arrangement of atoms constituting the compound semiconductor substrate 10 and the level of damage to induce emission of light. Therefore, the relationship can be evaluated in detail by use of the intensity ratio $(I_1/I_2)$. For example, the intensity ratio $(I_1/I_2)$ tends to decrease with increasing level of damage.

Method 4 is suitably applicable to production of compound semiconductor substrate 10. The compound semiconductor substrate 10 is determined to be nondefective when the intensity ratio $(I_1/I_2)$ is not less than a predetermined threshold; this permits the compound semiconductor substrate 10 with a low level of damage to be produced at a high yield.

<Method 5>

Method 5 is to perform evaluation of damage using the intensity $I_1$ of the peak $P_1$. For example, the intensity $I_1$ of the peak $P_1$ decreases with increasing level of damage. Method 5 is suitably applicable to production of compound semiconductor substrate 10. The compound semiconductor substrate 10 is determined to be nondefective when the intensity $I_1$ of the peak $P_1$ is not less than a predetermined threshold, relative to an intensity of a peak located at the wavelength $\lambda_1$ in an emission spectrum obtained by photoluminescence measurement on a surface of a compound semiconductor substrate from which damage is preliminarily eliminated; this permits the compound semiconductor substrate 10 with a low level of damage to be produced at a high yield.

When the compound semiconductor substrate 10 is made, for example, of a gallium nitride compound semiconductor, the intensity ratio $(I_1/I_2)$ is preferably not less than 2. In this case, a gallium nitride compound semiconductor substrate is obtained with a low level of damage on its surface.

When the compound semiconductor substrate 10 is made, for example, of a gallium nitride compound semiconductor, the intensity $I_1$ of the peak $P_1$ at the wavelength $\lambda_1$ (near 365 nm) is preferably not less than 1/10 of an intensity of a peak at the wavelength $\lambda_1$ (near 365 nm) in an emission spectrum obtained by photoluminescence measurement on a surface of a gallium nitride compound semiconductor substrate from which damage is eliminated (a gallium nitride compound semiconductor member without damage). In this case, a gallium nitride compound semiconductor substrate is obtained with a low level of damage on its surface.

Damage of compound semiconductor membrane 20 may also be evaluated instead of the compound semiconductor substrate 10. In this case, the photoluminescence measurement is preliminarily carried out on the surface 22a of the substrate 22, and the level of damage can be evaluated in detail on the surface 20a of the compound semiconductor membrane 20 provided on the substrate 22, by one of Method 1 to Method 4. Since the relative influence of damage on the compound semiconductor membrane 20 is greater, the damage can be detected easier even if the level of damage is low.

Furthermore, the compound semiconductor membrane 20 with a low level of damage can be produced at a high yield by use of Method 1 to Method 5. When the compound semiconductor membrane 20 is made, for example, of a gallium nitride compound semiconductor, the intensity ratio $(I_1/I_2)$ is preferably not less than 2. In this case, a gallium nitride compound semiconductor membrane is obtained with a low level of damage on its surface.

When the compound semiconductor membrane 20 is made, for example, of a gallium nitride compound semiconductor, the intensity $I_1$ of the peak $P_1$ at the wavelength $\lambda_1$ (near 365 nm) is preferably not less than 1/10 of an intensity of a peak at the wavelength $\lambda_1$ (near 365 nm) in an emission spectrum obtained by photoluminescence measurement on a surface of a gallium nitride compound semiconductor membrane from which damage is eliminated (a gallium nitride compound semiconductor member without damage). In this case, a gallium nitride compound semiconductor membrane is obtained with a low level of damage on its surface.

(Thin Film Forming Step)

Figure 5A:
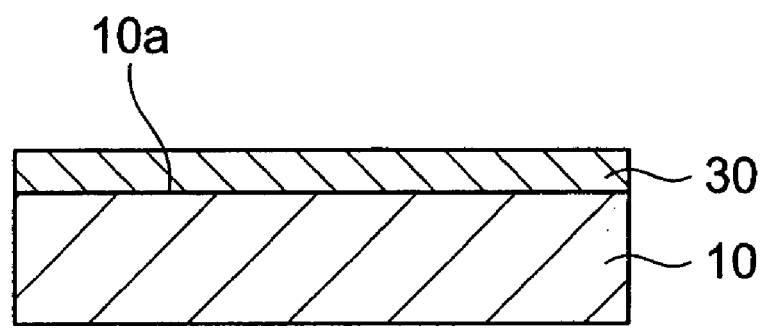
FIG. 5A is a sectional view schematically showing a compound semiconductor substrate in a thin film forming step.
Figure 5B:
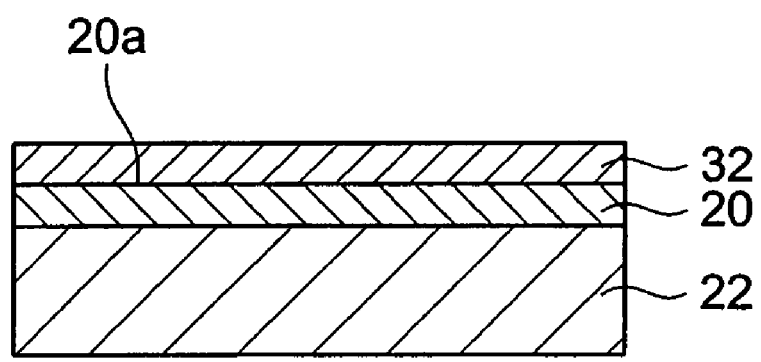
FIG. 5B is a sectional view schematically showing a compound semiconductor membrane in the thin film forming step.

FIG. 5A is a sectional view schematically showing a compound semiconductor substrate in the thin film forming step. FIG. 5B is a sectional view schematically showing a compound semiconductor membrane in the thin film forming step. The thin film forming step S3 is preferably carried out after the damage evaluation step S2.

The thin film forming step S3 is to form a thin film 30 on the surface 10a of the compound semiconductor substrate 10, as shown in FIG. 5A. The thin film 30 is formed, for example, by an epitaxial growth method. The thin film 30 can be a compound semiconductor film, an oxide film, a ZnO film, an amorphous film, or the like. When the thin film 30 is formed on the surface 10a of the compound semiconductor substrate 10 with a low level of damage, an improvement is made in crystallinity and surface roughness of the thin film 30. For example, in a case where the compound semiconductor substrate 10 is made of a gallium nitride compound semiconductor and where the intensity ratio $(I_1/I_2)$ is not less than 2, an improvement is made in crystallinity and surface roughness of the thin film 30 made of a gallium nitride compound semiconductor.

In addition, for example, in a case where the compound semiconductor substrate 10 is made of a gallium nitride compound semiconductor and where the intensity $I_1$ of the peak $P_1$ at the wavelength $\lambda_1$ (near 365 nm) is not less than 1/10 of an intensity of a peak at the wavelength $\lambda_1$ (near 365 nm) in an emission spectrum obtained by photoluminescence measurement on a surface of a gallium nitride compound semiconductor substrate from which damage is eliminated (a gallium nitride compound semiconductor member without damage), an improvement is made in crystallinity and surface roughness of the thin film 30 made of a gallium nitride compound semiconductor.

The thin film forming step S3 may also be to form a thin film 32 on the surface 20a of the compound semiconductor membrane 20, as shown in FIG. 5B. The thin film 32 is formed, for example, by an epitaxial growth method. The thin film 32 can be the same as the thin film 30. When the thin film 32 is formed on the surface 20a of the compound semiconductor membrane 20 with a low level of damage, an improvement is made in crystallinity and surface roughness of the thin film 32. For example, in a case where the compound semiconductor membrane 20 is made of a gallium nitride compound semiconductor and where the intensity ratio $(I_1/I_2)$ is not less than 2, an improvement is made in crystallinity and surface roughness of the thin film 32 made of a gallium nitride compound semiconductor.

In addition, for example, in a case where the compound semiconductor membrane 20 is made of a gallium nitride compound semiconductor and where the intensity $I_1$ of the peak $P_1$ at the wavelength $\lambda_1$ (near 365 nm) is not less than 1/10 of an intensity of a peak at the wavelength $\lambda_1$ (near 365 nm) in an emission spectrum obtained by photoluminescence measurement on a surface of a gallium nitride compound semiconductor membrane from which damage is eliminated (a gallium nitride compound semiconductor member without damage), an improvement is made in crystallinity and surface roughness of the thin film 32 made of a gallium nitride compound semiconductor.

(Electrode Forming Step)

Figure 6A:
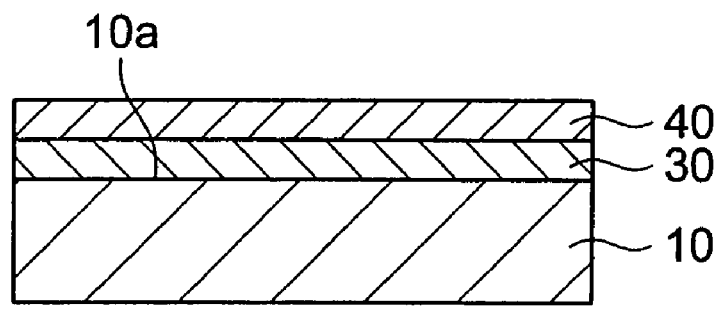
FIG. 6A is a sectional view schematically showing a compound semiconductor substrate in an electrode forming step.
Figure 6B:
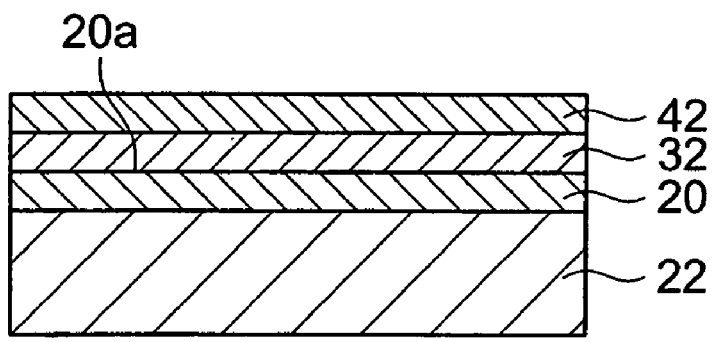
FIG. 6B is a sectional view schematically showing a compound semiconductor membrane in the electrode forming step.

FIG. 6A is a sectional view schematically showing a compound semiconductor substrate in the electrode forming step. FIG. 6B is a sectional view schematically showing a compound semiconductor membrane in the electrode forming step. The electrode forming step S4 is preferably carried out after the damage evaluation step S2 and more preferably carried out after the thin film forming step S3.

The electrode forming step S4 is to form an electrode 40, for example, of a metal film or the like on the thin film 30, as shown in FIG. 6A. In this case, the thin film 30 has excellent crystallinity and reduced surface roughness, and occurrence of damage can be suppressed at the interface between the thin film 30 and the electrode 40.

The electrode 40 may also be formed directly on the surface 10a of the compound semiconductor substrate 10. In that case, when the compound semiconductor substrate 10 with a low level of damage is used, occurrence of damage can be suppressed at the interface between the compound semiconductor substrate 10 and the electrode 40.

The electrode forming step S4 may also be to form an electrode 42 on the thin film 32, as shown in FIG. 6B. In this case, the thin film 32 has excellent crystallinity and reduced surface roughness, and occurrence of damage can be suppressed at the interface between the thin film 32 and the electrode 42.

The electrode 40 may also be formed directly on the surface 20a of the compound semiconductor membrane 20. In that case, when the compound semiconductor membrane 20 with a low level of damage is used, occurrence of damage can be suppressed at the interface between the compound semiconductor membrane 20 and the electrode 42.

A compound semiconductor device can be produced through the steps described above.

The preferred embodiments of the present invention were described above in detail, but it is noted that the present invention is not limited to the above embodiments.

Subsequently, Experiment Examples associated with the above embodiments will be described.

EXPERIMENT EXAMPLE 1

First, a monocrystalline GaN ingot was sliced to prepare a monocrystalline GaN substrate with the diameter of 2 inches. The surface of the monocrystalline GaN substrate prepared was polished and thereafter the surface was dry-etched by reactive ion etching (RIE). The conditions for dry etching were as follows.

Etching gas: Ar gas
Supplied power: 200 W
Pressure in chamber: 1.3 Pa (10 mTorr)
Etching time: 10 minutes Thereafter, in order to eliminate damage from the surface, the monocrystalline GaN substrate was immersed in a 5% $NH_4OH$ solution at 40° C. for 15 minutes to effect wet etching. The monocrystalline GaN substrate of Experiment Example 1 was obtained as described above.

EXPERIMENT EXAMPLE 2

First, a monocrystalline GaN ingot was sliced to prepare a monocrystalline GaN substrate with the diameter of 2 inches. The surface of the monocrystalline GaN substrate prepared was roughly polished and thereafter the surface was further polished by means of diamond abrasive grains with the grain size of 0.5 μm. Thereafter, the surface was cleaned with isopropyl alcohol. The monocrystalline GaN substrate of Experiment Example 2 was obtained as described above.

EXPERIMENT EXAMPLE 3

A monocrystalline GaN substrate of Experiment Example 3 was obtained in the same manner as in Experiment Example 2 except that diamond abrasive grains with the grain size of 0.1 μm were used instead of the diamond abrasive grains with the grain size of 0.5 μm.

EXPERIMENT EXAMPLE 4

A monocrystalline GaN substrate of Experiment Example 4 was obtained by effecting dry etching in Experiment Example 1 on a monocrystalline GaN substrate obtained in the same manner as in Experiment Example 3.

EXPERIMENT EXAMPLE 5

A monocrystalline GaN substrate of Experiment Example 5 was obtained by effecting wet etching with a diluted $H_3PO_4$ solution on a monocrystalline GaN substrate obtained in the same manner as in Experiment Example 4.

(Photoluminescence Measurement)

The photoluminescence measurement was conducted using a He—Cd laser that can emit a laser beam with the wavelength of 325 nm, as the light source 12. The laser beam is made incident normally to the surfaces of the monocrystalline GaN substrates of Experiment Example 1 to Experiment Example 5, to obtain their respective emission spectra. FIG. 7 shows an example of an emission spectrum.

FIG. 7 is a graph showing the emission spectrum obtained from the monocrystalline GaN substrate of Experiment Example 5. The vertical axis indicates the PL intensities (photoluminescence intensities) and the horizontal axis the wavelengths. In FIG. 7 the PL intensities are relative values with respect to 1 for the intensity $I_1$ of the peak $P_1$ near 365 nm. A broad peak $P_2$ appears near 470-640 nm on the longer wavelength side than 365 nm.

The photoluminescence measurement was carried out at wavelength intervals of 0.5 nm and values near the peak $P_1$ were interpolated by a Gaussian distribution. The background was adjusted by linear approximation of wing portions of the peak $P_1$.

(Evaluation of Damage)

Figure 8:
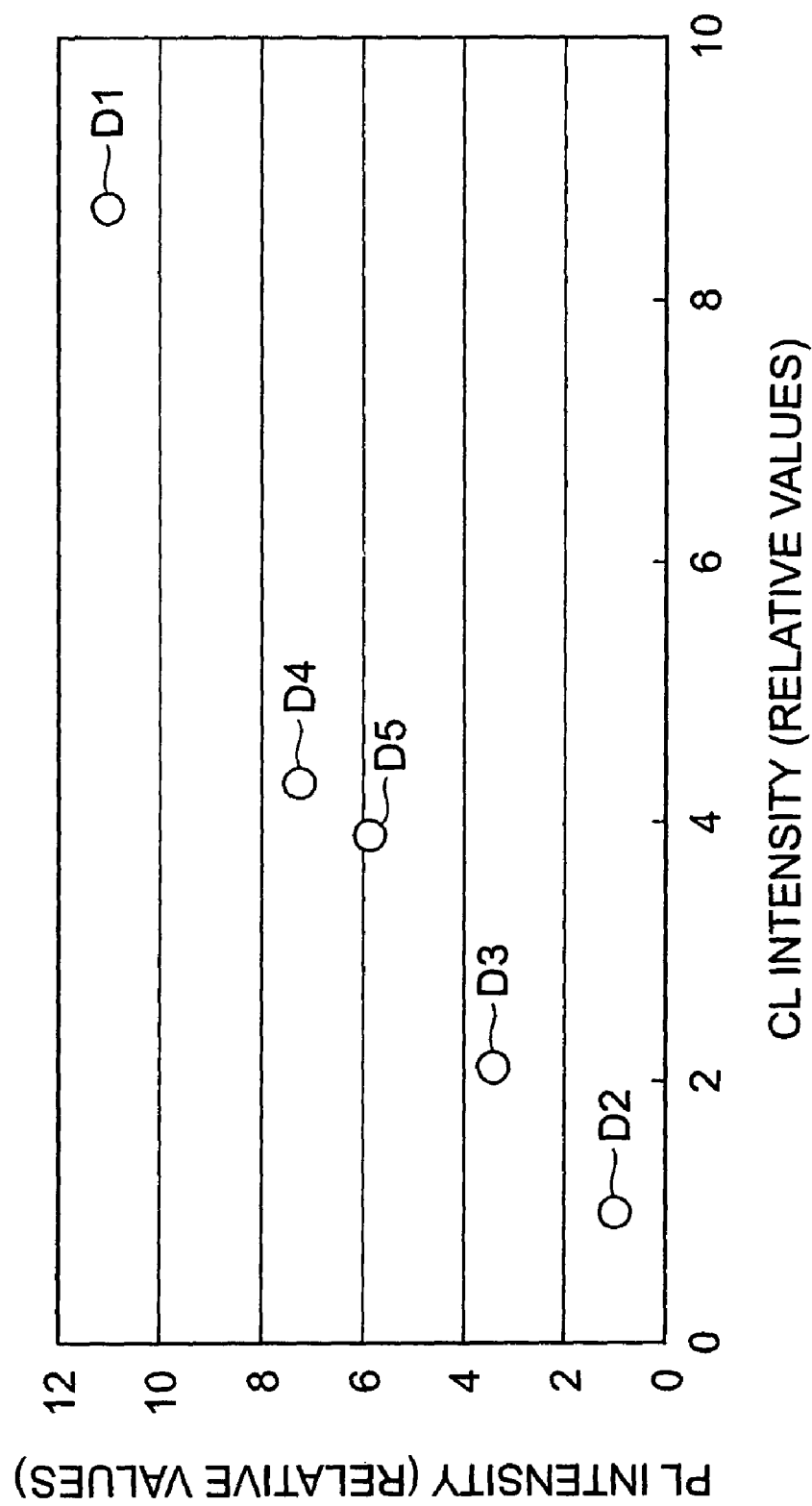
FIG. 8 is a graph showing a correlation between photoluminescence measurement and cathodoluminescence measurement.

FIG. 8 is a graph showing a correlation between photoluminescence measurement and cathodoluminescence measurement. The vertical axis indicates the PL intensities and the horizontal axis the CL intensities (cathodoluminescence intensities). In FIG. 8, plot D1 to plot D5 represent respective intensities $I_1$ of the peak $P_1$ near 365 nm in the emission spectra obtained from the monocrystalline GaN substrates of Experiment Example 1 to Experiment Example 5. The PL intensities are relative values with respect to 1 for the intensity $I_1$ of the peak $P_1$ near 365 nm in the emission spectrum obtained from the monocrystalline GaN substrate of Experiment Example 2. The CL intensities are also relative values with respect to 1 for the CL intensity in the monocrystalline GaN substrate of Experiment Example 2.

It is seen from FIG. 8 that there is a correlation between the photoluminescence measurement and the cathodoluminescence measurement. In general, the CL intensity decreases with increasing level of damage, and it is thus seen that the PL intensity also decreases with increasing level of damage.

FIG. 9 shows the intensities $I_1$ of the peak $P_1$ near 365 nm in the emission spectra obtained from the monocrystalline GaN substrates of Experiment Example 1 to Experiment Example 5. It is seen from FIG. 9 that the level of damage on the surface increases in the order of Experiment Example 1, Experiment Example 4, Experiment Example 5, Experiment Example 3, and Experiment Example 2.

Table 1 shows the half width $W_1$ of the peak $P_1$ near 365 nm in each of the emission spectra obtained from the monocrystalline GaN substrates of Experiment Example 1 to Experiment Example 5. It is seen from Table 1 that the half width $W_1$ of the peak $P_1$ increases with increasing level of damage.

TABLE 1

|  | Half Width $W_1$ of Peak $P_1$ [nm] |
|---|---|
| Experiment Example 2 | 10.6 |
| Experiment Example 3 | 9.7 |
| Experiment Example 5 | 8.4 |
| Experiment Example 4 | 8.1 |
| Experiment Example 1 | 7.1 |

Table 2 shows the intensity $I_2$ and half width $W_2$ of the peak $P_2$ in each of the emission spectra obtained from the monocrystalline GaN substrates of Experiment Example 1 to Experiment Example 5. It is seen from Table 2 that the intensity $I_2$ and half width $W_2$ of the peak $P_2$ both increase with increasing level of damage.

TABLE 2

|  | Intensity $I_2$ of Peak $P_2$ | Half Width $W_2$ of Peak $P_2$[nm] |
| --- | --- | --- |
| Experiment Example 2 | 1 | 142 |
| Experiment Example 3 | 0.86 | 137 |
| Experiment Example 5 | 0.31 | 134 |
| Experiment Example 4 | 0.25 | 105 |
| Experiment Example 1 | 0.11 | 101 |

Table 3 shows the intensity ratio ($I_1/I_2$) in each of the emission spectra obtained from the monocrystalline GaN substrates of Experiment Example 1 to Experiment Example 5. It is seen from Table 3 that the intensity ratio ($I_1/I_2$) decreases with increasing level of damage.

TABLE 3

|  | Intensity Ratio ($I_1/I_2$) |
| --- | --- |
| Experiment Example 2 | 1 |
| Experiment Example 3 | 4 |
| Experiment Example 5 | 19 |
| Experiment Example 4 | 28 |
| Experiment Example 1 | 100 |

EXPERIMENT EXAMPLE 6

A monocrystalline GaN substrate of Experiment Example 6 without damage was obtained in the same manner as in Experiment Example 1, except that the substrate used was a monocrystalline GaN substrate 20 mm square.

EXPERIMENT EXAMPLE 7

A monocrystalline GaN ingot was sliced to prepare a monocrystalline GaN substrate 20 mm square. The surface of the monocrystalline GaN substrate prepared was roughly polished and thereafter the surface was further polished by means of diamond abrasive grains with the grain size of 0.3 μm, to obtain the monocrystalline GaN substrate of Experiment Example 7.

EXPERIMENT EXAMPLE 8

A monocrystalline GaN substrate of Experiment Example 8 was obtained in the same manner as in Experiment Example 7 except that diamond abrasive grains with the grain size of 0.8 μm were used instead of the diamond abrasive grains with the grain size of 0.3 μm.

(Photoluminescence Measurement)

The photoluminescence measurement was carried out on the surfaces of the monocrystalline GaN substrates of Experiment Example 6 to Experiment Example 8. Table 4 shows the intensity $I_1$ of the peak $P_1$ and the intensity ratio ($I_1/I_2$) in each of the emission spectra obtained from the monocrystalline GaN substrates of Experiment Example 6 to Experiment Example 8. It is seen from the intensity $I_1$ of the peak $P_1$ that the level of damage on the surface increases in the order of Experiment Example 6, Experiment Example 7, and Experiment Example 8. Therefore, it is seen that the intensity ratio ($I_1/I_2$) decreases with increasing level of damage.

TABLE 4

|  | Intensity $I_1$ of Peak $P_1$ | Intensity Ratio ($I_1/I_2$) |
| --- | --- | --- |
| Experiment Example 6 | 1 | 102 |
| Experiment Example 7 | 0.31 | 2.4 |
| Experiment Example 8 | 0.09 | 1 |

Next, a thin film of GaN was formed in the thickness of 1 μm by HVPE on the surfaces of the monocrystalline GaN substrates of Experiment Example 6 to Experiment Example 8. The conditions for formation of the GaN thin film are presented below. GaCl gas is obtained by reaction of Ga metal with HCl gas at 880° C.
Temperature of monocrystalline GaN substrate: 1000° C.
Reaction gases: $NH_3$ gas and GaCl gas
Pressure of $NH_3$ gas: 10 kPa
Pressure of GaCl gas: 0.6 Pa After the thin film of GaN was formed, surface roughness of the GaN thin film (Ra: arithmetic mean roughness) was measured by AFM. A percentage of lattice strain to the bulk was measured by X-ray diffraction. Table 5 shows the measurement results of these. It was seen from Table 5 that the monocrystalline GaN substrates of Experiment Example 6 and Experiment Example 7 had satisfactory performance as substrates to be used for the compound semiconductor devices.

TABLE 5

|  | Arithmetic Mean Roughness[nm] | Percentage of Lattice Strain[%] |
| --- | --- | --- |
| Experiment Example 6 | 0.82 | 0.01 |
| Experiment Example 7 | 0.99 | 0.05 |
| Experiment Example 8 | 1.61 | 0.17 |

The present invention provides the damage evaluation methods of the compound semiconductor member permitting the detailed evaluation of the level of damage on the surface and the production methods of the compound semiconductor member with a low level of damage, and also provides the gallium nitride compound semiconductor members and gallium nitride compound semiconductor membranes with a low level of damage.

What is claimed is:

1. A gallium nitride substrate on which a device is to be formed, wherein:
    the gallium nitride substrate has a gallium nitride (GaN) bandgap,
    the gallium nitride substrate has a front surface,
    the front surface has a surface damage such a level that, when a laser light having a wavelength shorter than a wavelength corresponding to the GaN bandgap is irradiated to the front surface of the gallium nitride substrate, a photoluminescence emission PL1 having a wavelength corresponding to the GaN bandgap and a photoluminescence emission PL2 having a wavelength between 470 nm to 640 nm are obtained, and an intensity of the PL1 is not less than twice an intensity of the PL2.
2. The gallium nitride substrate according to claim 1, wherein the gallium nitride substrate includes a base substrate on which the gallium nitride substrate is disposed.

3. A gallium nitride compound semiconductor membrane formed on the gallium nitride substrate according to claim 1.

4. The gallium nitride substrate according to claim 1, wherein a wavelength of a peak of the PL1 exists near 365 nm.

5. The gallium nitride substrate according to claim 1, wherein the damage is caused by a polishing or etching process.

6. A compound semiconductor substrate comprising:
the gallium nitride substrate according to claim 1; and
an epitaxial layer formed on the front surface of the gallium nitride substrate.

\* \* \* \* \*